United States Patent
Gu et al.

(10) Patent No.: US 9,204,843 B2
(45) Date of Patent: *Dec. 8, 2015

(54) OPTICAL DISTANCE MEASUREMENT SYSTEM AND OPERATION METHOD THEREOF

(75) Inventors: Ren-Hau Gu, Hsin-Chu (TW); Chi-Chieh Liao, Hsin-Chu (TW); Ming-Tsan Kao, Hsin-Chu (TW); Sen-Huang Huang, Hsin-Chu (TW)

(73) Assignee: PIXART IMAGING INC., Hsin-Chu (TW)

( * ) Notice: Subject to any disclaimer, the term of this patent is extended or adjusted under 35 U.S.C. 154(b) by 599 days.

This patent is subject to a terminal disclaimer.

(21) Appl. No.: 13/613,664

(22) Filed: Sep. 13, 2012

(65) Prior Publication Data

US 2013/0131473 A1 May 23, 2013

(30) Foreign Application Priority Data

Nov. 18, 2011 (TW) .............................. 100142235 A

(51) Int. Cl.
*A61B 5/1455* (2006.01)
*A61B 5/00* (2006.01)
*G06F 3/042* (2006.01)

(52) U.S. Cl.
CPC ........... *A61B 5/6886* (2013.01); *A61B 5/14552* (2013.01); *A61B 5/6826* (2013.01); *A61B 5/7203* (2013.01); *G06F 3/0421* (2013.01); *G06F 3/0425* (2013.01); *A61B 5/7207* (2013.01); *A61B 2560/0223* (2013.01)

(58) Field of Classification Search
CPC .............. A61B 5/6886; A61B 5/6826; A61B 5/14552; A61B 5/7203; A61B 5/0205; A61B 5/7214; A61B 5/02433; A61B 5/14551; A61B 5/7207; A61B 5/02416
See application file for complete search history.

(56) References Cited

U.S. PATENT DOCUMENTS

| | | | |
|---|---|---|---|
| 5,983,120 A * | 11/1999 | Groner et al. | 600/310 |
| 5,990,866 A * | 11/1999 | Yollin | 345/157 |
| 6,327,376 B1 | 12/2001 | Harkin | |
| 7,072,701 B2 | 7/2006 | Chen et al. | |
| 7,697,966 B2 * | 4/2010 | Monfre et al. | 600/310 |
| 2008/0306366 A1 | 12/2008 | Ohki et al. | |
| 2010/0305418 A1* | 12/2010 | Deliwala | 600/324 |
| 2011/0199337 A1 | 8/2011 | Tang et al. | |

FOREIGN PATENT DOCUMENTS

| | | |
|---|---|---|
| CN | 101317757 A | 12/2008 |
| CN | 101554328 A | 10/2009 |
| TW | 397918 B | 7/2000 |
| TW | 200817651 A | 4/2008 |
| TW | 201128489 A | 8/2011 |

* cited by examiner

*Primary Examiner* — Eric Winakur
(74) *Attorney, Agent, or Firm* — Hauptman Ham, LLP

(57) ABSTRACT

There is provided an operation method of an optical distance measurement system including a first mode and a second mode. The first mode is configured to detect a finger distance. The second mode is configured to detect a physiological characteristic, wherein the optical distance measurement system transfers from the first mode to the second mode when the finger distance is within a predetermined range. There is further provided an optical distance measurement system.

21 Claims, 6 Drawing Sheets

OPTICAL DISTANCE MEASUREMENT SYSTEM AND OPERATION METHOD THEREOF

CROSS REFERENCE TO RELATED APPLICATION

This application claims the priority benefit of Taiwan Patent Application Serial Number 100142235, filed on Nov. 18, 2011, the full disclosure of which is incorporated herein by reference.

BACKGROUND

1. Field of the Disclosure

This disclosure generally relates to a human interface system and, more particularly, to an optical distance measurement system and operation method thereof having the function of detecting physiological characteristics of a user.

2. Description of the Related Art

Conventional optical distance measurement systems utilize a light sensor, such as a proximity sensor or an ambient light sensor to detect the intensity variation of ambient light so as to detect a relative distance and control the operation of an electronic device, e.g. temporarily turning ON/OFF a specific function, according to the relative distance. Presently, the optical distance measurement system has been widely applied to various electronic devices such as cell phones, tablet personal computers and personal digital assistants. With the development of industry, users spend more and more time on utilizing various portable electronic devices that puts a lot of stress on their bodies. However, conventional optical distance measurement systems are not able to detect the current physiological status of the user.

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variation of the penetrating light of the two wavelengths is detected, the blood oxygenation can be calculated according to equation (1):

$$\text{Oxygen saturation} = 100\% \times [HbO_2]/([HbO_2]+[Hb]) \quad (1)$$

wherein $[HbO_2]$ is an oxyhemoglobin concentration; and $[Hb]$ is a deoxy-hemoglobin concentration.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the physiology information such as the oxyhemoglobin and deoxyhemoglobin concentration, respectively. Finally, the blood oxygenation can be calculated according to equation (1).

However, as conventional pulse oximeters detect the intensity variation of the penetrating light, different intensity signals will be detected by detecting different parts of the human body. In addition, when the part of the human body being detected has a movement, a disturbed signal can be detected such that it is not possible to calculate correct physiology information. Therefore, conventional pulse oximeters cannot be applied to electronic devices operated in a moving state.

Accordingly, the present disclosure provides an optical distance measurement system and an operation method of the optical distance measurement system capable of detecting physiological characteristics of a user configured to detect a finger distance, a finger motion and physiological characteristics, wherein the signal noise caused by the finger movement can be eliminated in detecting the physiological characteristics.

SUMMARY

It is an object of the present disclosure to provide an optical distance measurement system and operation method thereof that may detect a finger distance and a finger motion, and may detect a physiological characteristic of a user when the finger distance is within a predetermined range.

It is another object of the present disclosure to provide a control chip of an optical distance measurement system that may detect a finger distance, a finger motion and a physiological characteristic of a user by analyzing reflected light from a finger, and may output the encoded, sequenced and/or compressed finger distance, finger motion and physiological characteristic.

It is another object of the present disclosure to provide an optical distance measurement system and operation method thereof that may detect a finger distance, a finger motion and a physiological characteristic of a user, and has a mechanism of eliminating the interference from ambient light sources.

It is another object of the present disclosure to provide an optical distance measurement system and operation method thereof that may detect a finger distance, a finger motion and a physiological characteristic of a user, and has the denoising mechanism.

It is another object of the present disclosure to provide an optical distance measurement system and operation method thereof that may detect a finger distance, a finger motion and a physiological characteristic of a user, and may compensate the frequency drift caused by temperature variations.

It is another object of the present disclosure to provide an optical distance measurement system and operation method thereof that may detect a finger distance, a finger motion and a physiological characteristic of a user, and may enter a sleep mode after idling for a predetermined time period.

The present disclosure provides an optical distance measurement system configured to detect a finger distance and a physiological characteristic. The optical distance measurement system includes a first light source, a second light source, a light control unit, an image sensor and a processing unit. The first light source provides light of a first wavelength to a finger. The second light source provides light of a second wavelength to the finger. The light control unit is configured to control on-states of the first light source and the second light source. The image sensor receives reflected light from the finger at a sampling frequency to generate a plurality of first image frames corresponding to the on-states of the first light source and a plurality of second image frames corresponding to the on-states of the second light source. The processing unit is configured to calculate the finger distance according to the first image frames or the second image frames and to calculate the physiological characteristic according to the first image frames and the second image frames when the finger distance is within a predetermined range.

The present disclosure further provides an operation method of an optical distance measurement system including a first mode and a second mode. The first mode is configured to detect a finger distance. The second mode is configured to detect a physiological characteristic, wherein the optical distance measurement system transfers from the first mode to the second mode when the finger distance is within a predetermined range.

The present disclosure further provides an operation method of an optical distance measurement system including: providing light of a first wavelength or a second wavelength to a finger surface; receiving reflected light of the first wavelength or the second wavelength to generate a plurality of image frames; calculating a finger distance according to an intensity distribution of the image frames; and performing following steps when the finger distance is within a predetermined range: providing light of the first wavelength and the second wavelength to the finger surface; using an image sensor to receive reflected light of the first wavelength to generate a plurality of first image frames and to receive reflected light of the second wavelength to generate a plurality of second image frames; dividing each of the first image frames and each of the second image frames into at least two parts and calculating an average brightness of each part; analyzing the average brightness of the each part of the first image frames to obtain a first intensity variation and analyzing the average brightness of the each part of the second image frames to obtain a second intensity variation; and calculating a blood oxygenation according to the first intensity variation and the second intensity variation.

In the embodiments of the present disclosure, when the finger distance is within the predetermined range, each of the first image frames is divided into at least two parts and an average brightness of each part is calculated; and the average brightness of the each part of the first image frames is analyzed to obtain a first intensity variation using independent component analysis or blind source separation. And each of the second image frames is divided into at least two parts and an average brightness of each part is calculated; and the average brightness of the each part of the second image frames is analyzed to obtain a second intensity variation using independent component analysis or blind source separation. And the physiological characteristic is calculated according to the first intensity variation and the second intensity variation.

In the optical distance measurement system and operation method thereof, the processing unit further detects a finger motion according to an intensity variation of the image frames, such as detecting a waving direction of the finger.

In the optical distance measurement system and the operation method of the present disclosure, the physiological characteristic may include a blood oxygenation and a heart rate. In the present disclosure, the movement informant and the physiology information are separated by means of independent component analysis (ICA) or blind source separation (BSS) so as to effectively eliminate the signal noise caused by the finger movement.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
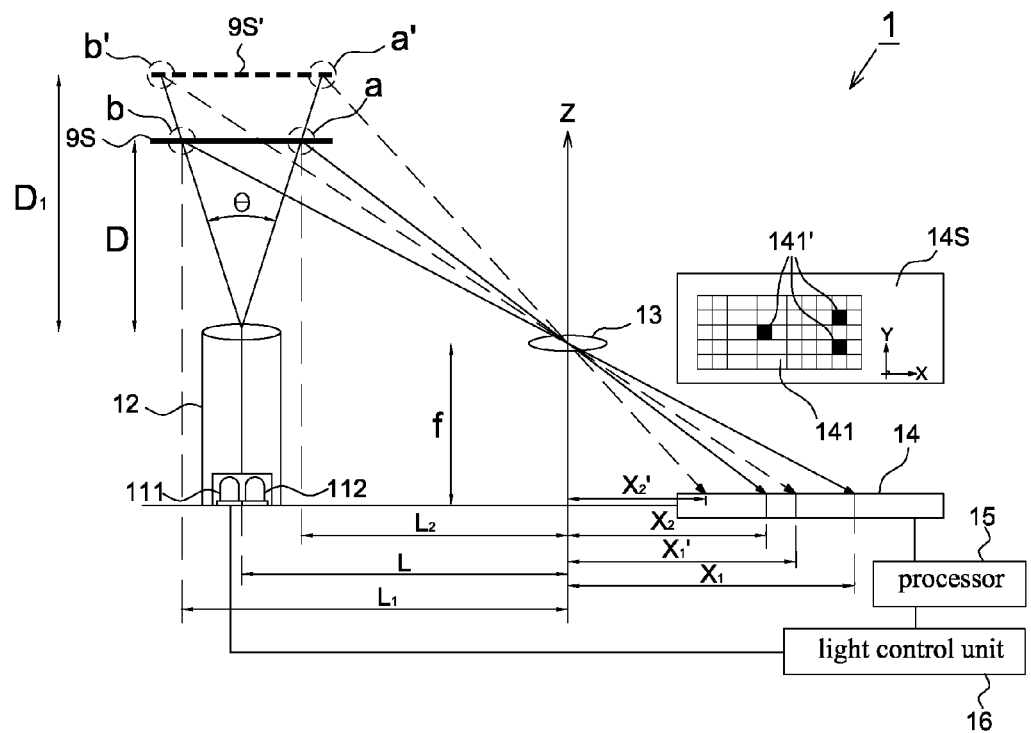
FIG. 2A shows a schematic diagram of the optical distance measurement system according to an embodiment of the present disclosure.

Please refer to FIG. 2A, it shows a schematic diagram of the optical distance measurement system according to an embodiment of the present disclosure. The optical distance measurement system 1 includes two operation modes. In a first mode, the optical distance measurement system 1 is configured to detect a finger distance and a finger motion. In a second mode, the optical distance measurement system 1 is configured to detect a physiological characteristic (e.g. including a blood oxygenation and a heart rate) of a user, wherein the first mode and the second mode may be switched by a user using a change-over switch, or may be switched when the finger distance is within a predetermined range (i.e. distance range). For example, the first mode is entered when the finger distance in not within the predetermined range, and the second mode is entered when the finger distance is within the predetermined range. Said predetermined range may be determined according to different applications.

The optical distance measurement system 1 includes two light sources 111-112, a first light guide 12, a second light guide 13, an image sensor 14, a processing unit 15 and a light control unit 16. It should be mentioned that the spatial relationship between every component in FIG. 2A is only exemplary and not to limit the present disclosure. The light sources 111-112 may be light emitting diodes or laser diodes and are configured to respectively emit light of different wavelengths to a finger surface 9S (the finger is not shown in the figure for simplification). Preferably, said different wavelengths are the two wavelengths used in conventional pulse oximeters, e.g. red light of wavelength about 660 nm and infrared light of wavelength about 905, 910 or 940 nm It is appreciated that the wavelengths mentioned herein are the center wavelength of respective illumination spectrum of the light sources 111-112.

The first light guide 12 is configured to direct the light emitted by the light sources 111 and 112 toward a predetermined direction (e.g. toward the front of the light sources 111 and 112 herein). In other embodiments, if the light emitted by the light sources 111 and 112 can propagate toward the predetermined direction, the first light guide 12 may not be implemented.

The second light guide 13 is configured to direct the light reflected from the finger surface 9S to the image sensor 14. In one embodiment, the second light guide 13 may be a lens having a focal length f and is configured to focus the reflected from the finger surface 9S on the image sensor 14 so as to increase the sensing efficiency thereof. It is appreciated that the structure and the light guiding mechanism of the first light guide 12 and the second guide 13 are not limited to those shown in FIG. 2A.

The image sensor 14 receives, with a sampling parameter, reflected light from the finger surface 9S to generate a plurality of image frames, which may have a plurality of pixels such as 16×16 pixels, wherein the sampling parameter may include an exposure time and an image gain, e.g. an analog gain or a digital gain, but not limited thereto. The image sensor 14 is preferably an active matrix sensor, e.g. a CMOS image sensor.

The processing unit 15 calculates a finger distance and a finger motion of a finger 9 and a physiological characteristic of a user according to the plurality of image frames outputted by the image sensor 14. The finger distance, finger motion and physiological characteristic obtained by the processing unit 15 may be wired or wirelessly sent to an electronic device having at least one response unit for displaying or corresponding control, wherein the response unit may be a monitor, a lamp device, a seven-segment display and/or a sound device. The electronic device may be a portable electronic device or a home appliance.

The light control unit 16 is coupled to the processing unit 15 and configured to control on-states and off-states of the light sources 111-112 corresponding to the image capturing of the image sensor 14, and details thereof will be described hereinafter.

Figure 2B:
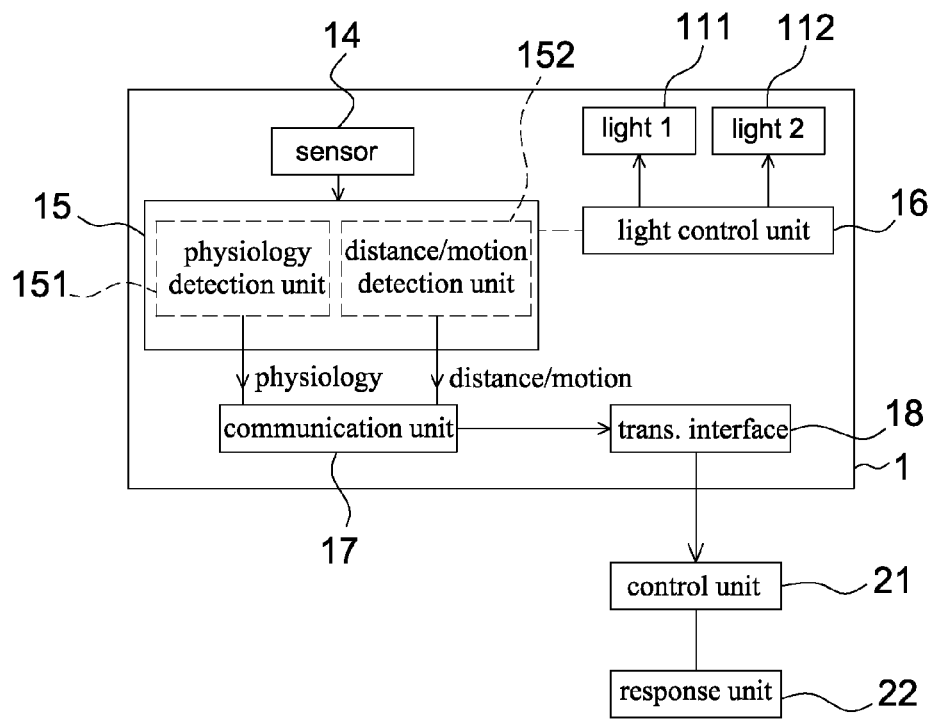
FIG. 2B shows a schematic block diagram of the optical distance measurement system according to an embodiment of the present disclosure.

Please refer to FIGS. 2A and 2B, FIG. 2B shows a schematic block diagram of the optical distance measurement system according to an embodiment of the present disclosure. The optical distance measurement system 1 includes a first light source 111, a second light source 112, the image sensor 14, the processing unit 15, the light control unit 16, a communication unit 17 and a transmission interface 18. Because the processing unit 15 has multifunction, the processing unit 15 may include a physiology detection unit 151 configured to detect a physiological characteristic of the finger 9 and include a distance/motion detection unit 152 configured to detect the finger distance and the finger motion. That is, the processing unit 15 may be a single element or composed of two elements.

The first light source 111 may emit red light of wavelength about 660 nm to the finger 9, and the second light source 112 may emit infrared light of wavelength about 905, 910 or 940 nm to the finger 9. Broadly speaking, the first light source 111 and the second light source 112 may respectively emit light of the two wavelengths used in conventional pulse oximeters. The light control unit 16 controls the first light source 111 and the second light source 112 to emit light. The image sensor 14 receives reflected light associated with the first light source 111 and/or the second light source 112 from the finger surface 9S. The communication unit 17 is configured to perform at least one of an encoding process, a sequential process and a compressing process on the finger distance, finger motion, and/or physiological characteristic obtained by the processing unit 15 and send processed results to the transmission interface 18 for transmission. The transmission interface 18 is configured to wired or wirelessly transmit the encoded, sequenced and/or compressed finger distance, finger motion and/or physiological characteristic to an external control unit 21, wherein the wired and wireless communication techniques are well known and thus details thereof are not described herein. The control unit 21 may be coupled to an electronic device having at least one response unit 22 and is configured to control the electronic device to display and/or respond the received finger distance, finger motion and/or physiological characteristic by means of the response unit 22 or to control the electronic device to temporarily disable or enable a specific function. The control unit 21 may be integrated in the response unit 22 or separated from the response unit 22.

The optical distance measurement system 1 of the present disclosure may incorporate with an electronic device having a response unit 22 such that a user may control a software executed and/or images displayed by the response unit 22 using the optical distance measurement system 1, and the response unit 22 may give a warning when the physiological characteristic indicates that the user is in a fatigue or excitatory state (e.g. according to a value of the physiological characteristic), wherein the method of showing the physiological characteristic and the warning may be implemented by, for example, displaying on a screen, representing by a lamp device or by sound controlled by a software. For example, the response unit 22 may show the physiological characteristic (at least one of the blood oxygenation and the heart rate) and generate a warning state when the physiological characteristic exceeds a predetermined value, such as reducing the darkness of the screen, inserting an image object or playing a sound, but not limited thereto.

In one embodiment, the optical distance measurement system 1 may include two image sensors configured to detect light of two different wavelengths respectively emitted by the light sources 111 and 112 (i.e. the image sensor 14 is replaced by two image sensors), wherein an optical bandpass filter may be integrated on one or two of the image sensors in order to select the desired spectrum.

When the optical distance measurement system 1 is activated, the first mode is automatically entered. In the first mode, the light control unit 16 controls, according to a predetermined definition, one of the first light source 111 and the second light source 112 to emit light to illuminate a finger surface 9S. The reflected light from the finger surface 9S may impinge on the image sensor 14 after passing through the second light guide 13. The image sensor 14 captures and outputs a plurality of image frames at a sampling frequency. The processing unit 15 calculates a finger distance and a finger motion according to the image frames, e.g. calculating the finger distance according to an intensity distribution of the image frames and calculating the finger motion according to an intensity variation of the image frames. For example, when the finger surface (shown as 9S) is located at a first distance D, reflected light from a first end "a" and a second end "b" of an illuminated area θ of the finger surface 9S is respectively reflected to image positions $X_2$ and $X_1$ after passing through the second light guide 13. Meanwhile, the first distance D may be obtained according to the distance parameter of the system "L", the focal length "f", the distance parameters of the illuminated area "$L_1$" and "$L_2$", the image positions "$X_1$"

and "$X_2$'" using triangulation. For example when the finger surface (shown as 9S') is located at a second distance $D_1$, reflected light from a first end "a'" and a second end "b'" of an illuminated area θ of the finger surface 9S' is respectively reflected to image positions $X_2$' and $X_1$' after passing through the second light guide 13. Meanwhile, the second distance $D_1$ may be obtained according to the distance parameter of the system "L", the focal length "f", the distance parameters of the illuminated area "$L_1$" and "$L_2$", the image positions "$X_1$'" and "$X_2$'" using triangulation. That is, the finger distance may be obtained according to intensity distributions of the reflected light from the finger surface 9S or 9S', and the first mode is continuously functioning when the finger distance is not within a predetermined range.

As shown in FIG. 2A, a sensing array is formed on a sensing surface 14S of the image sensor 14 including a plurality of sensing pixels 141 arranged in a pixel array. In this manner, when a finger enters a illuminated area θ of the light sources 111 and 112 from outside of the illuminated area θ, the plurality of sensing pixels 141 of the sensing array receive different intensity distributions of the reflected from the finger surface at different time intervals, and thus the processing unit 15 may identify the finger motion according to the intensity variation of the intensity distributions. It is appreciated that the image sensor 14 may include a plurality of sensing pixels separated apart from each other such as the filled three sensing pixels 141' shown in FIG. 2A. And the processing unit 15 may also be able to detect the finger distance and the finger motion according to the intensity distribution and the intensity variation respectively.

When the processing unit 15 identifies that the finger distance is within a predetermined range, the second mode is entered. In the second mode, the light control unit 16 controls the first light source 111 and the second light source 112 to emit light alternatively or simultaneously so as to illuminate the finger surface 9S. The image sensor 14 receives reflected light from the finger surface 9S at a sampling frequency to generate a plurality of first image frames corresponding to on-states of the first light source and generate a plurality of second image frames corresponding to on-states of the second light source. The processing unit 15 then calculates the physiological characteristic according to the first image frames and the second image frames.

As the method of calculating the finger distance and the finger motion by the processing unit 15 (or the distance/motion detection unit 152) according to the intensity variation and the intensity distribution of the sensing pixels 141 is well known, details thereof are not described herein. Only the method of calculating the physiological characteristic by the processing unit 15 (or the physiology detection unit 151) in the second mode will be described hereinafter.

Sampling Mechanism

The optical distance measurement system 1 of the present disclosure utilizes two light sources 111 and 112 and may perform two functions simultaneously, wherein the function of detecting the finger distance and the finger motion may use the image frames associated with any wavelength without limitation, but the function of detecting the physiological characteristic needs to be respectively performed corresponding to the image frames of different wavelengths. First, the sampling mechanism of the image frames in the present disclosure is illustrated hereinafter.

Figure 3:
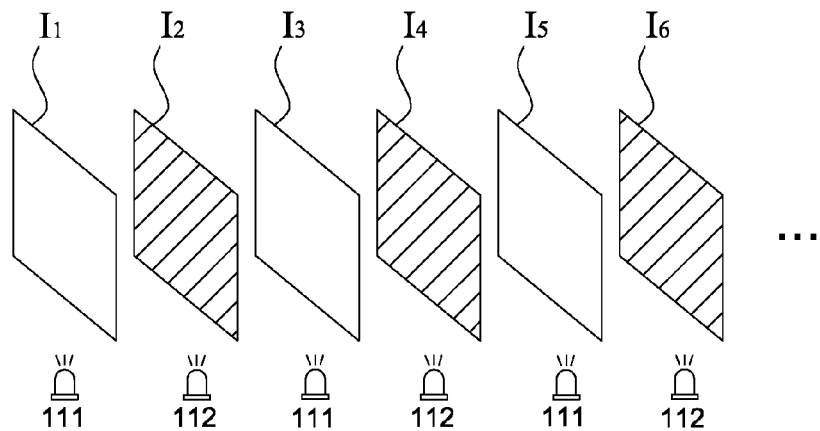
FIG. 3 shows a schematic diagram of the image frames captured by the image sensor in the second mode of the optical distance measurement system according to the embodiment of the present disclosure.

In one embodiment of the second mode, the light control unit 16 controls the first light source 111 and the second light source 112 to turn on alternatively. The image sensor 14 captures image frames at a high and fixed sampling frequency (e.g. 3,000 frames/sec) and synchronizing to the turning on (i.e. on-states) of the first light source 111 or the second light source 112, and outputs a plurality of image frames $I_1$ to $I_6$ . . . as shown in FIG. 3 to the processing unit 15 (or the physiology detection unit 151), wherein the image frames $I_1$ to $I_6$ . . . include first image frames $I_1$, $I_3$, $I_5$ . . . corresponding to the on-states of the first light source 111 and second image frames $I_2$, $I_4$, $I_6$ . . . corresponding to the on-states of the second light source 112. That is, the processing unit 15 alternatively outputs the first image frames and the second image frames.

The processing unit 15 may calculate an intensity variation of first image frame according to the first image frames $I_1$, $I_3$, $I_5$ . . . , and calculate an intensity variation of second image frame according to the second image frames $I_2$, $I_4$, $I_6$ . . . (described later), and accordingly calculate the absorptivity of blood in two spectra so as to obtain [$HbO_2$] and [Hb]. Finally, the blood oxygenation may be calculated according to equation (1), and a heart rate may also be calculated according to a comparison result of comparing the intensity variation of first image frame and/or the intensity variation of second image frame with at least one pulse threshold.

Figure 4:
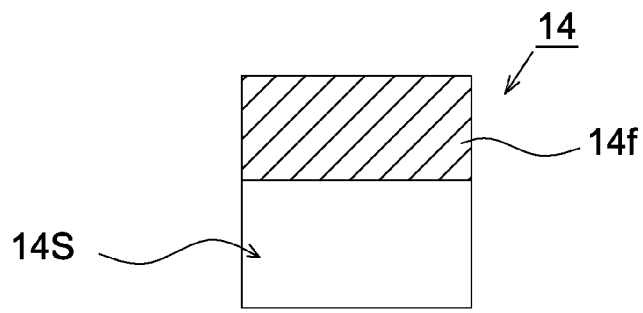
FIG. 4 shows a schematic diagram of the image sensor of the optical distance measurement system according to the embodiment of the present disclosure, wherein an optical filter is disposed in front of a part of a sensing surface thereof.

In another embodiment of the second mode, the light control unit 16 controls the first light source 111 and the second light source 112 to turn on simultaneously and to synchronize to the image capturing of the image sensor 14; that is, the image sensor 14 may receive reflected light of two wavelengths simultaneously. Therefore, in this embodiment an optical filter 14f is preferably disposed in front of at least a part of a sensing surface 14S of the image sensor 14 as shown in FIG. 4, wherein the optical filter 14f may be an optical bandpass filter to allow the part of the sensing surface 14S behind the optical filter 14f to only receive the spectrum of light of the first light source 111 or the second light source 112 such that the processing unit 15 may distinguish the first image frame (i.e. the part of the image frame associated with the first light source 111) and the second image frame (i.e. the part of the image frame associated with the second light source 112). It is appreciated that in the present disclosure the position and the area of the optical filter 14f are not limited to those shown in FIG. 4.

In this manner, the processing unit 15 may also calculate the intensity variation of first image frame according to the first image frames $I_1$, $I_3$, $I_5$ . . . , calculate the intensity variation of second image frame according to the second image frames $I_2$, $I_4$, $I_6$ . . . , and calculate at least one of the blood oxygenation and the heart rate according to the two intensity variations.

It is appreciated that as the sensing efficiency of the image sensor 14 toward light of different wavelengths may be different or the illumination brightness values of the first light source 111 and the second light source 112 may not be exactly identical, the brightness value of the image frames captured by the image sensor 14 may be previously adjusted (e.g. adjusting the sampling parameter, such as an exposure time and an image gain, of the image frames corresponding to different wavelengths) before the shipment of the optical distance measurement system 1 such that the image frames initially outputted by the image sensor 14 may have substantially identical brightness values so as to eliminate the possibility of error.

In this embodiment, the light control unit 16 controls the first light source 111 and the second light source 112 such that the image sensor 14 captures reflected light from the finger 9 at a sampling frequency to generate a plurality of first image frames corresponding to on-states of the first light source 111 and a plurality of second image frames corresponding to on-states of the second light source 112. The processing unit 15 calculates the physiological characteristic according to the first image frames and the second image frames.

Mechanism of Eliminating Ambient Light Interference

In FIG. 2A, the ambient light outside the optical distance measurement system 1 can be received by the image sensor 14 to degrade the image quality of the image frames captured thereby. In the present disclosure, the light control unit 16 may control the first light source 111 and the second light source 112 to turn off (i.e. the off-state) in predetermined time intervals.

Figure 5:
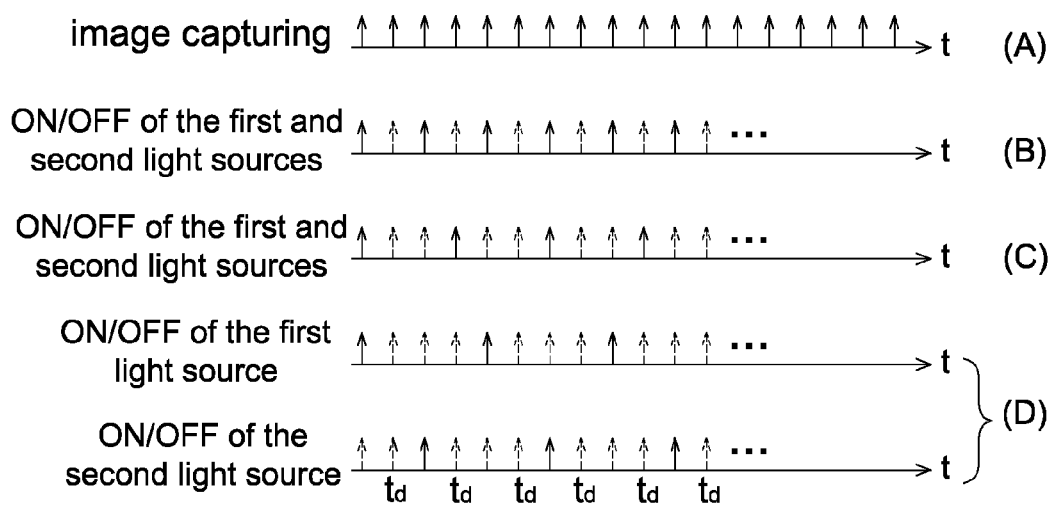
FIG. 5 shows a schematic diagram of the image capturing of the image sensor and the ON/OFF of the light source in the second mode of the optical distance measurement system according to the embodiment of the present disclosure.

For example please refer to FIG. 5, it shows a schematic diagram of the image capturing of the image sensor 14 and the ON/OFF of the first light source 111 and the second light source 112, wherein in FIGS. 5(B)-5(D) solid arrows denote the on-states of the light sources (or the lighting at a first brightness value) and dashed arrows denote the off-states of the light sources (or the lighting at a second brightness value), and the second brightness value may be smaller than the first brightness value. FIG. 5(A) shows that the image sensor 14 captures image frames at a fixed sampling frequency. FIG. 5(B) shows that the first light source 111 and the second light source 112 are alternatively turned on and turned off at the same time, and thus the image sensor 14 may alternatively capture bright image frames (i.e. corresponding to the on-states or the first brightness value of the light sources) and dark image frames (i.e. corresponding to the off-states or the second brightness value of the light sources). FIG. 5(C) shows that the first light source 111 and the second light source 112 are simultaneously turned on once after being turned off two image periods, and this case is generally for a lower displacement of the finger 9. As mentioned above, when the first light source 111 and the second light source 112 are turned on simultaneously, e.g. FIGS. 5(B) and 5(C), the image sensor 14 further includes an optical filter 14$f$ (as shown in FIG. 4) for spatially distinguishing the image frame associated with different light sources such that one part of the image sensor 14 may sense reflected light associated with the first light source 111 and the other part thereof may sense reflected light associated with the second light source 112.

When the finger 9 enters the illuminated area 0, the bright image frames, which are associated with the on-states of the light sources, include components of (reflected light from finger+stray light+ambient light), and the dark image frames, which are associated with the off-states of the light sources, include only the component of (ambient light). Therefore, if a dark image frame is subtracted from a bright image frame, the interference from the ambient light can be effectively eliminated. The processing unit 15 may calculate the physiological characteristic according to differential images between the bright image frames and the dark image frames.

Please refer to FIG. 5(D), it shows an embodiment in which the first light source 111 and the second light source 112 are turned on alternatively. In this embodiment, in order to allow the image sensor 14 to be able to capture dark image frames, the light control unit 16 controls the first light source 111 and the second light source 112 to alternatively turn on every other image frame, e.g. the two light sources are both turned off at time $t_d$ in FIG. 5(D). Accordingly, the processing unit 15 may calculate a differential first image (i.e. bright first image frame—dark image frame) and a differential second image (i.e. bright second image frame—dark image frame), and calculate the physiological characteristic according to the differential first and second images. As mentioned above, if the first light source 111 and the second light source 112 are turned on alternatively, the image sensor 14 temporally distinguishes the image frames associated with different light sources.

In this embodiment, the light control unit 16 controls the first light source 111 and the second light source 112 to turn on simultaneously or alternatively and the image sensor 14 is able to capture dark image frames when both the light sources are turned off. The interference from ambient light is eliminated by calculating a difference between the bright image frame and the dark image frame. It is appreciated that the on-states and the off-states of each light source shown in FIG. 5 are only exemplary and not to limit the present disclosure.

Denoising Mechanism

As the image frames captured by the image senor 14 generally include noise which is randomly distributed in the image frames being captured. Therefore, in the present disclosure it is able to calculate a sum of M image frames to increase the signal-to-noise ratio (SNR) thereby improving the calculation accuracy of the physiological characteristic. For example, it is able to calculate a sum of 10 image frames and two groups of 10 image frames may have partially repeated image frames or totally different 10 image frames. It is appreciated that if the first light source 111 and the second light source 112 are turned on alternatively, the sum of image frames in this embodiment may be a sum of the first image frames (e.g. $I_1+I_3+I_5+\ldots$ as shown in FIG. 3) and a sum of the second image frames (e.g. $I_2+I_4+I_6+\ldots$ as shown in FIG. 3) since two intensity variations need to be calculated respectively. However, if the first light source 111 and the second light source 112 are turned on simultaneously, the sum of image frames in this embodiment is a sum of successive image frames (e.g. $I_1+I_2+I_3+I_4+I_5+I_6+\ldots$ as shown in FIG. 3), and the two intensity variations may be spatially distinguished by post-processing. In addition, if the mechanism of eliminating ambient light interference described above is incorporated in this embodiment, the sum of image frames in this embodiment is a sum of the differential images; that is, the process of eliminating ambient light interference is performed and then the process of denoising is performed successively. In other embodiments, only one of the mechanism of eliminating ambient light interference and the denoising mechanism is performed.

As mentioned above, the image sensor 14 may capture image frames with different sampling parameters at different conditions, e.g. the image sensor 14 may have different absorption of light at different wavelengths. Therefore different sampling parameters, such as different exposure times and different image gains, may be used to make the first image frames and the second image frames have substantially identical initial brightness values in order to correctly perform the post-processing on the image frames; that is, the sampling parameters associated with the first image frames and the second image frames may be different. In the present disclosure, in order to eliminate the influence of different sampling parameters, every image frame or the sum of M image frames or the average of M image frames may be normalized by the sampling parameter, e.g. (one image frame/sampling parameter), (a sum of M image frames/sampling parameter) or (an average of M image frames/sampling parameter), wherein M is a positive integer.

Calculating Physiological Characteristics

Corresponding to the on-states of different light sources, the image frames captured by the image sensor 14 may contain physiology information and finger movement information at the same time. Therefore, in the present disclosure the processing unit 15 (or the physiology detection unit 151) has to separate two types of information at first and then is able to calculate the physiological characteristic correctly. In the present disclosure, the processing unit 15 may separate the two types of information according to, for example, independent component analysis (ICA) or blind source separation (BSS).

Figure 1:
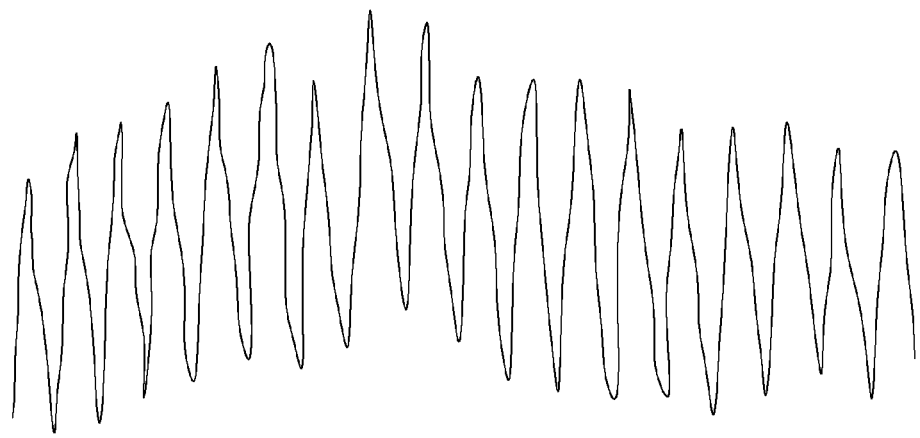
FIG. 1 shows a schematic diagram of an intensity variation of the penetrating light detected by pulse oximeters.
Figure 6:
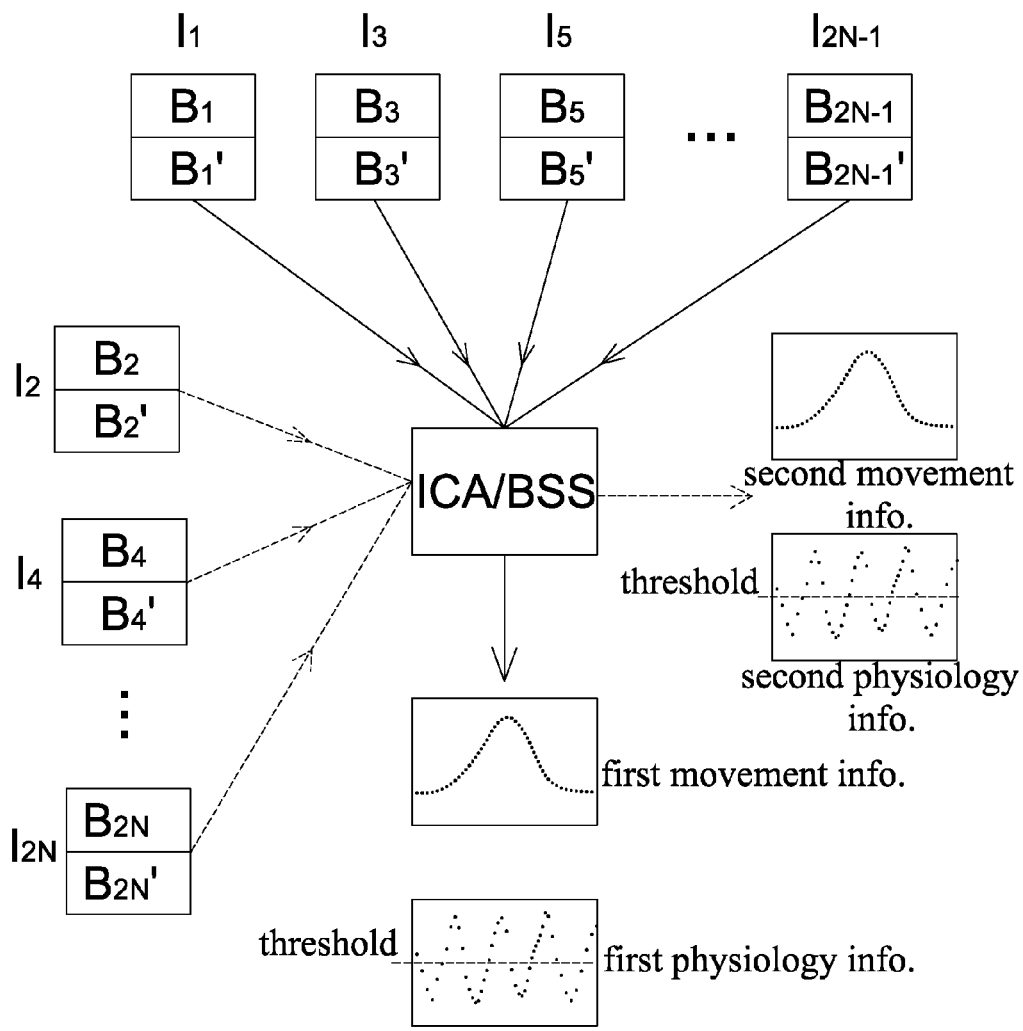
FIG. 6 shows a schematic diagram of separating the movement information and the physiology information by the processing unit in the second mode of the optical distance measurement system according to the embodiment of the present disclosure.

Please refer to FIGS. 3 and 6, taking the first image frames $I_1, I_3, I_5 \ldots$ shown in FIG. 3 as an example, each of the first image frames (e.g. original first image frames or the first image frames processed by the mechanism of eliminating ambient light interference and/or normalizing mechanism) or each of the sum of a plurality of first image frames (e.g. a sum of M original first image frames or a sum of M first image frames processed by the mechanism of eliminating ambient light interference and/or normalizing mechanism) is divided into at least two parts and an average brightness of each part is calculated, e.g. the image frame $I_1$ is divided into two parts respectively having an average brightness $B_1$ and $B_1'$; the image frame $I_3$ is divided into two parts respectively having an average brightness $B_3$ and $B_3'$; ...; the image frame $I_{2N-1}$ is divided into two parts respectively having an average brightness $B_{2N-1}$ and $B_{2N-1}'$, wherein the image frames may be divided into more than two parts in other embodiments. Next, a first movement informant and a first physiology information may be separated from the divided image frames according to independent component analysis (ICA) or blind source separation (BSS) method as shown in FIG. 6, and each of the information is shown as a curve of intensity variation. In the present disclosure the movement information is abandoned and the physiological characteristic is calculated only according to the physiology information (i.e. the intensity variation of image frame). It is appreciated that as the sampling frequency of the image sensor 14 is much higher than the heart rate, the separated physiology information is shown as a curve of the intensity variation in accordance with the pulse beating (i.e. similar to FIG. 1), but the separated movement information is not limited to that shown in FIG. 6. In addition, the two parts divided from the image frames are not necessary to be the upper and the lower parts of the image frames. In addition, as it is necessary to respectively calculate the physiology information associated with two different wavelengths, the aforementioned separation process is performed respectively on the first image frames $I_1, I_3, I_5 \ldots$ (i.e. corresponding to the on-state of the first light source) and the second image frames $I_2, I_4, I_6 \ldots$ (i.e. corresponding to the on-state of the second light source) such that a second movement information and a second physiology information can be retrieved from the second image frames $I_2, I_4, I_6 \ldots$, wherein the second movement information is abandoned and the intensity variation of the second physiological information is kept. It should be mentioned that, if the information separation is performed on the sum or average of the image frames, each of $I_1$ to $I_{2N-1}$ and $I_2$ to $I_{2N}$ shown in FIG. 6 represents a sum or an average of M image frames or normalized results thereof.

The ICA and BSS methods are mainly configured to separate combined signals. When the separated movement information is abandoned, it is able to eliminate the signal noise caused by the finger movement.

In the present embodiment, the processing unit 15 further calculates a heart rate according to a comparison result of comparing at least one pulse threshold with a first intensity variation (i.e. the first physiology information) and/or a second intensity variation (i.e. the second physiology information).

Sleep Mode

The optical distance measurement system 1 of the present disclosure may enter a sleep mode after idling for a predetermined time period. For example, when the processing unit 15 identifies that a finger 9 does not enter the illuminated area θ within the predetermined time period, the sleep mode is entered. In the sleep mode, the image capturing of the image sensor 14, the lighting of the light sources 111 and 112 and the operation of other active components may be disabled.

Calibration Mechanism

Generally in optical systems, temperature variations can cause the frequency drift of the system frequency and the light source frequency. The processing unit of the optical distance measurement system 1 of the present disclosure may further have the calibration mechanism to compensate the error due to the temperature variations mentioned above so as to increase the system accuracy.

The physiology detection method of the optical distance measurement system 1 according to reflected light from the finger surface 9S includes the steps of: providing light of a first wavelength or a second wavelength to a finger surface (Step $S_{11}$); capturing reflected light of the first wavelength or the second wavelength to generate a plurality of image frames (Step $S_{12}$); calculating a finger distance according to an intensity distribution of the image frames (Step $S_{13}$); identifying whether the finger distance is within a predetermined range (Step $S_{14}$); if yes, executing the following steps: providing light of a first wavelength and a second wavelength to a finger surface (Step $S_{141}$; capturing reflected light of the first wavelength to generate a plurality of first image frames and capturing reflected light of the second wavelength to generate a plurality of second image frames (Step $S_{142}$); dividing each of the first image frames and each of the second image frames into at least two parts and calculating an average brightness of each part (Step $S_{143}$); using independent component analysis or blind source separation to analyze the average brightness of the each part of the first image frames to obtain a first intensity variation and to analyze the average brightness of the each part of the second image frames to obtain a second intensity variation (Step $S_{144}$); and calculating a physiological characteristic according to the first intensity variation and the second intensity variation (Step $S_{145}$); if the finger distance is not within the predetermined range, returning to Step $S_{11}$. In this embodiment, the Steps $S_{11}$~$S_{13}$ are referred to the first mode, and the Steps $S_{141}$~$S_{145}$ are referred to the second mode. In addition, the Step $S_{13}$ may further include calculating a finger motion according to an intensity variation of the image frames. Details of every step have been described above and thus are not repeated herein.

Figure 8:
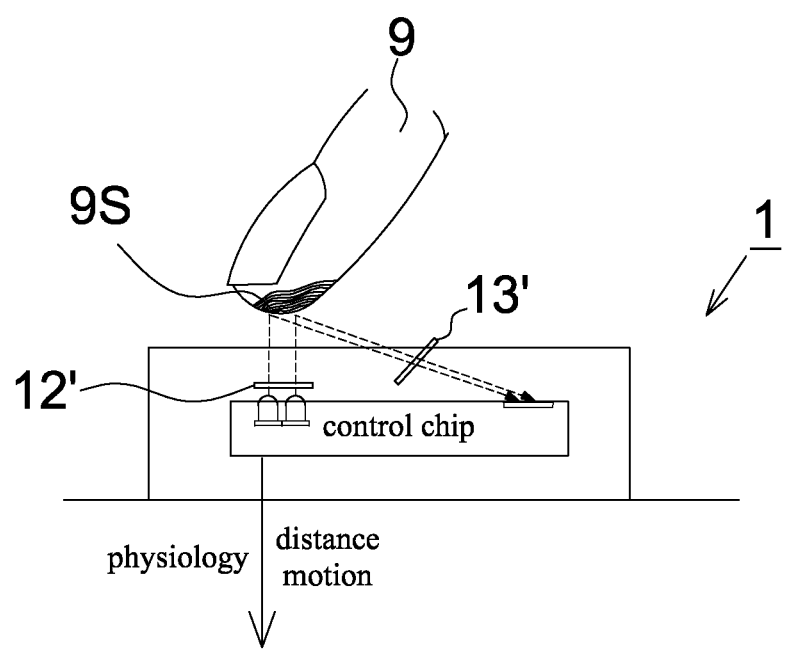
FIG. 8 shows a schematic diagram of the optical distance measurement system according to another embodiment of the present disclosure.

In another embodiment, a part of or all of the light sources 111-112, the image sensor 14, the processing unit 15, the light control unit 16, the communication unit 17 and the transmission interface 18 may be manufactured as a control chip or a package as shown in FIG. 8. The control chip or the package is configured to detect a finger distance and a finger motion in the first mode, and enters the second mode when the finger distance is within a predetermined distance. The control chip or the package is configured to detect a physiological characteristic of the finger 9 in the second mode, and to output encoded, sequenced and/or compressed finger distance, finger motion and/or physiological characteristic, wherein the methods of calculating the finger distance, finger motion and/or physiological characteristic have been described above and thus details thereof are not repeated herein. It is appreciated that the disposition of every element of the optical distance measurement system shown in FIG. 8 is only exemplary and not to limit the present disclosure. In other embodiments, said compressing process may be performed by an additional compression unit.

Figure 7:
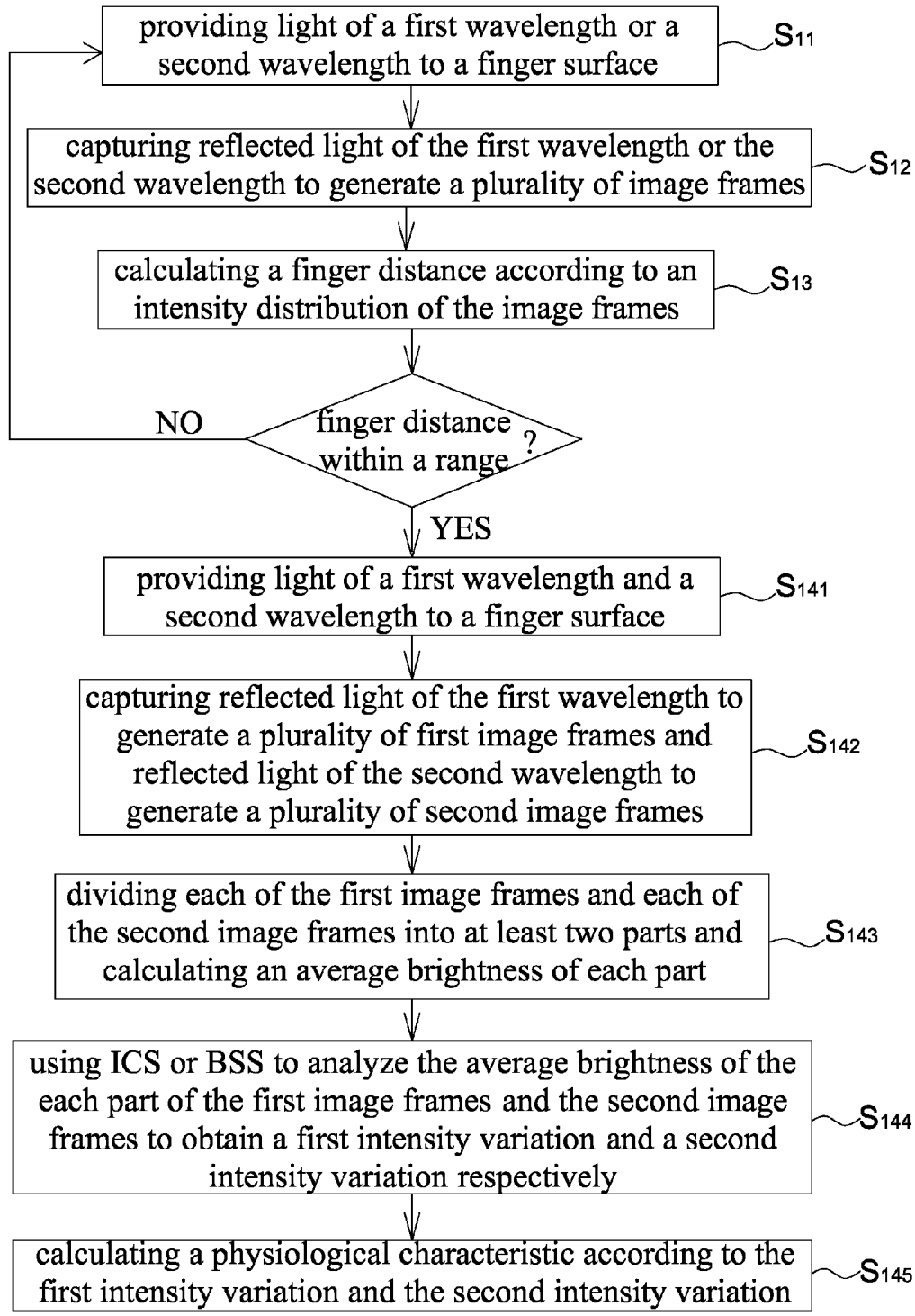
FIG. 7 shows a flow chart of the physiology detection method according to an embodiment of the present disclosure.

As mentioned above, the conventional optical distance measurement system can not detect the physiological characteristic of a user and the method of calculating the blood oxygenation for pulse oximeters cannot be applied to an optical distance measurement system since it can not detect a moving object. Therefore, the present disclosure further provides an optical distance measurement system (FIGS. 2A, 2B and 8) and operation method thereof (FIG. 7) wherein the optical distance measurement system may detect both the finger information and the physiology information, and may control a response unit to update images to be displayed according to the finger information and to display the physiology information. The optical distance measurement system in the embodiments of the present disclosure may eliminate the signal noise caused by finger movement and the interference from ambient light sources, and further has the mechanism of entering sleep mode.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An optical distance measurement system configured to detect a finger distance of a finger of a user from the optical distance measurement system and a physiological characteristic of the user, the optical distance measurement system comprising:
   a first light source configured to provide light of a first wavelength to the finger;
   a second light source configured to provide light of a second wavelength to the finger;
   a light control unit configured to control on-states of the first light source and the second light source;
   an image sensor configured to receive reflected light from the finger at a sampling frequency to generate a plurality of first image frames corresponding to the on-states of the first light source and a plurality of second image frames corresponding to the on-states of the second light source; and
   a processing unit configured to
      calculate the finger distance and a finger motion of the finger according to the first image frames or the second image frames, and
      calculate the physiological characteristic according to the first image frames and the second image frames when the finger distance is within a predetermined range, wherein
      the finger motion is not calculated when the finger distance is within the predetermined range.

2. The optical distance measurement system as claimed in claim 1, wherein when the finger distance is within the predetermined range, the processing unit is configured to
   divide each of the first image frames into at least two parts and calculate an average brightness of each part, and analyze the average brightness of the each part of the first image frames to obtain a first intensity variation;
   divide each of the second image frames into at least two parts and calculate an average brightness of each part, and analyze the average brightness of the each part of the second image frames to obtain a second intensity variation; and
   calculate the physiological characteristic according to the first intensity variation and the second intensity variation.

3. The optical distance measurement system as claimed in claim 2, wherein the processing unit is further configured to calculate a heart rate according to a comparison of at least one pulse threshold with at least one of the first intensity variation and the second intensity variation.

4. The optical distance measurement system as claimed in claim 1, wherein the physiological characteristic comprises a blood oxygenation and a heart rate.

5. The optical distance measurement system as claimed in claim 1, wherein when the finger distance is within the predetermined range,
   the light control unit is configured to alternatively enable the on-states of the first light source and the second light source such that the image sensor receives the reflected light associated with the first light source and the second light source alternatively; or
   the light control unit is configured to simultaneously enable the on-states of the first light source and the second light source such that the image sensor receives the reflected light associated with the first light source and the second light source simultaneously, and the image sensor comprises an optical filter covering at least a part of a sensing surface thereof.

6. The optical distance measurement system as claimed in claim 1, wherein the first light source, the second light source, the light control unit, the image sensor and the processing unit are packaged as a control chip to output the finger distance and the physiological characteristic processed by at least one of an encoding process, a sequential process and a compressing process.

7. The optical distance measurement system as claimed in claim 1, wherein the processing unit is configured to calculate the finger motion when the finger distance is not within the predetermined range.

8. The optical distance measurement system as claimed in claim 1, wherein the light control unit is configured to enable the on-states of one of the first light source and the second light source when the finger distance is not within the predetermined range.

9. The optical distance measurement system as claimed in claim 1, wherein the image sensor comprises a pixel array or a plurality of sensing pixels separated apart configured to detect the reflected light from the finger.

10. The optical distance measurement system as claimed in claim 1, wherein the processing unit is further configured to compensate errors caused by temperature variations.

11. An operation method of an optical distance measurement system, comprising:
   detecting a finger distance of a finger of a user from the optical distance measurement system and a finger motion of the finger in a first mode; and
   detecting a physiological characteristic of the user in a second mode,
   wherein the optical distance measurement system transfers from the first mode to the second mode when the finger distance is within a predetermined range and the finger motion is not detected when the finger distance is within the predetermined range.

12. The operation method as claimed in claim 11, wherein the second mode further comprises:
   providing light of a first wavelength and a second wavelength to a finger surface of the finger;
   receiving, by an image sensor, reflected light of the first wavelength to generate a plurality of first image frames and receiving reflected light of the second wavelength to generate a plurality of second image frames;
   dividing each of the first image frames and each of the second image frames into at least two parts and calculating an average brightness of each part;

analyzing the average brightness of the each part of the first image frames to obtain a first intensity variation and analyzing the average brightness of the each part of the second image frames to obtain a second intensity variation; and calculating the physiological characteristic according to the first intensity variation and the second intensity variation.

13. The operation method as claimed in claim 12, further comprising:

calculating a heart rate according to a comparison of at least one pulse threshold with at least one of the first intensity variation and the second intensity variation.

14. The operation method as claimed in claim 11, further comprising:

showing the physiological characteristic by a response unit; and generating a warning state when the physiological characteristic exceeds a predetermined value.

15. The operation method as claimed in claim 11, wherein the first mode further comprises:

illuminating a finger surface of the finger;

receiving reflected light from the finger surface to generate a plurality of image frames; and calculating the finger distance according to an intensity distribution of the image frames.

16. The operation method as claimed in claim 15, further comprising:

detecting the finger motion according to an intensity variation of the image frames.

17. The operation method as claimed in claim 11, further comprising:

performing at least one of an encoding process, a sequential process and a compressing process on the finger distance or the physiological characteristic.

18. An operation method of an optical distance measurement system, comprising:

providing light of a first wavelength or a second wavelength to a finger surface of a finger;

receiving reflected light of the first wavelength or the second wavelength to generate a plurality of image frames;

calculating a finger distance of the finger from the optical distance measurement system according to an intensity distribution of the image frames; and performing the following steps when the finger distance is within a predetermined range:

providing light of the first wavelength and the second wavelength to the finger surface;

receiving, by an image sensor, reflected light of the first wavelength to generate a plurality of first image frames and receiving reflected light of the second wavelength to generate a plurality of second image frames;

dividing each of the first image frames and each of the second image frames into at least two parts and calculating an average brightness of each part;

analyzing the average brightness of the each part of the first image frames to obtain a first intensity variation and analyzing the average brightness of the each part of the second image frames to obtain a second intensity variation; and calculating a blood oxygenation according to the first intensity variation and the second intensity variation.

19. The operation method as claimed in claim 18, wherein, when the finger distance is within the predetermined range, the operation method further comprises:

calculating a heart rate according to a comparison of at least one pulse threshold with at least one of the first intensity variation and the second intensity variation.

20. The operation method as claimed in claim 19, further comprising:

showing, by a response unit, at least one of the blood oxygenation and the heart rate; and generating a warning state when the blood oxygenation or the pulse rate exceeds a predetermined value.

21. The operation method as claimed in claim 18, further comprising:

detecting a finger motion of the finger according to an intensity variation of the image frames.

* * * * *